US009212126B2

(12) United States Patent
Moore et al.

(10) Patent No.: US 9,212,126 B2
(45) Date of Patent: Dec. 15, 2015

(54) PROCESS FOR THE PREPARATION OF NITROALCOHOLS

(71) Applicant: Angus Chemical Company, Buffalo Grove, IL (US)

(72) Inventors: David W. Moore, Hebron, IL (US); G. David Green, Cary, IL (US)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 0 days.

(21) Appl. No.: 14/379,798

(22) PCT Filed: Feb. 7, 2013

(86) PCT No.: PCT/US2013/025092
§ 371 (c)(1),
(2) Date: Aug. 20, 2014

(87) PCT Pub. No.: WO2013/133925
PCT Pub. Date: Sep. 12, 2013

(65) Prior Publication Data
US 2015/0038746 A1 Feb. 5, 2015

Related U.S. Application Data

(60) Provisional application No. 61/607,769, filed on Mar. 7, 2012.

(51) Int. Cl.
*C07C 201/12* (2006.01)
(52) U.S. Cl.
CPC ................... *C07C 201/12* (2013.01)
(58) Field of Classification Search
None
See application file for complete search history.

(56) References Cited

U.S. PATENT DOCUMENTS

2011/0105804 A1* 5/2011 Major et al. .................. 568/704

FOREIGN PATENT DOCUMENTS

| CN | 1765872 A | * | 5/2006 | ............ C07C 209/34 |
| WO | 2009/129097 A1 | | 10/2009 | |

OTHER PUBLICATIONS

Database CASREACT in STN, AN 145:145394, RX(5) of 26, CN 1765872, (May 3, 2006).*
Machine translation of CN 1765872 a (performed Feb. 18, 2015 online using Google Patents http://www.google.com/patents/CN1765872A?cl=en).*
Ishige et al., Bulletin of the Chemical Society of Japan, vol. 44, 1971, pp. 1917-1922.
Kobylinski et al., Journal of Catalysis, 17, 1970, pp. 384-393.
Leseticky et al., Collection Czechoslov. Chem. Commun., vol. 38, 1973, pp. 459-464.
Licht et al., Journal of Catalysis, 61, 1980, pp. 109-114.
Maier et al., Org. Chem., vol. 37B, No. 3, 1982, pp. 392-394.
Pines et al., Journal of Catalysis, 10, 1968, pp. 60-68.
Pines et al, Journal of Catalysis, 17, 1970, pp. 375-383.
International Preliminary Report on Patentability for PCT/US2013/025092, mailed Mar. 4, 2014.
International Search Report and Written Opinion on PCT/US2013/025092, mailed May 6, 2013.

* cited by examiner

*Primary Examiner* — Brian J Davis
(74) *Attorney, Agent, or Firm* — Foley & Lardner LLP

(57) ABSTRACT

A process of preparing a nitroalcohol, e.g., 2-nitro-2-methyl-1-propane, from a nitropolyol, e.g., 2-nitro-2-methyl-1,3-propanediol, the process comprising the step of contacting under hydrogenation conditions the nitropolyol with hydrogen, a hydrogenation catalyst and, optionally, a chelating agent.

16 Claims, No Drawings

PROCESS FOR THE PREPARATION OF NITROALCOHOLS

BACKGROUND OF THE INVENTION

1. Field of the Invention

This invention relates to a process of producing nitroalcohols by the reductive dehydroxylation of nitropolyols. In one aspect, the invention is a process of producing nitroalcohols by first alkylating a nitroalkane to a nitropolyol, and then hydrogenating the nitropolyol to a nitroalcohol.

2. Description of the Related Art

Nitroalkanes are used as feedstocks to prepare nitroalcohols which can be further reduced to aminoalcohols. Commercially, 2-nitro-2-methyl-1-propanol (NMP) and the corresponding aminoalcohol (2-amino-2-methyl-1-propanol (AMP)) are produced from 2-nitropropane (2-NP). The ability to produce identical products from alternative feedstocks, e.g., nitroethane, is desirable.

Reductive dehydroxylation is known for activated alcohols, e.g., benzylic alcohols. It has not been documented for nitropolyols such as the 1,2-nitroalcohols.

SUMMARY OF THE INVENTION

While attempting to reduce 2-nitro-2-methyl-1,3-propanediol (NMPD) to a hydroxylamine analogue, gas chromatography (GC) analysis of the reaction product showed that most of the starting material had been converted. Analysis by gas chromatography/mass spectroscopy (GC/MS) revealed the surprising result that a hydroxyl group had been cleaved and the starting material, 2-nitro-2-methyl-1,3-propanediol, was converted to the nitro-mono alcohol, 2-nitro-2-methyl-1-propanol. This was an unexpected result because a nitroalcohol with one hydroxyl group that is subjected to the same hydrogenation conditions is unaffected.

In one embodiment the invention is a process to cleave a hydroxyl group(s) from a nitropolyol. The process is the reaction of a nitropolyol under hydrogen pressure in the presence of a hydrogenation catalyst. The process is also useful in the manufacture of NMP and AMP using alternative nitroalkane feedstocks such as nitroethane or nitromethane.

In one embodiment the invention is a process of preparing a nitroalcohol from a nitropolyol, the process comprising the step of contacting under hydrogenation conditions a nitropolyol with hydrogen, a hydrogenation catalyst and, optionally, a chelating agent.

In one embodiment the invention is a process of preparing a nitroalcohol from a nitroalkane, the process comprising the steps of:
A. Contacting under alkaline conditions a nitroalkane, an aldehyde and an alkaline catalyst to form a nitropolyol, and
B. Contacting under hydrogenation conditions the nitropolyol of A with hydrogen, a hydrogenation catalyst and, optionally, a chelating agent.

The process of this invention allows for the preparation of NMP and AMP (both industrially useful compounds) from a nitroalkane feedstock other than 2-NP. This alternative route to NMP and AMP is useful to those not interested in investing the capital to make 2-NP and that have a readily-available nitromethane or nitroethane feedstock.

DETAILED DESCRIPTION OF THE PREFERRED EMBODIMENT

Definitions

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, temperature, etc., is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the reaction temperature and pressure.

"Hydrogenation conditions" and like terms mean the temperature and pressure under which a nitropolyol is converted to a nitroalcohol in the presence of hydrogen, a hydrogenation catalyst, a solvent and, optionally, a chelating agent. These conditions are dependent upon a host of factors including, but not limited to, the nitropolyol, the hydrogenation catalyst and the amount of hydrogenation catalyst, the solvent, the presence or absence of a chelating agent and if a chelating agent is present, then its chemical composition. Typically the temperature is 25° C. to 120° C., more typically 60° C. to 100° C., and typically the pressure is 300 psi (2,068 kPa) to 1,400 psi (9,653 kPa), more typically 500 psi (3,447 kPa) to 800 psi (5,516 kPa).

"Alkaline conditions" and like terms mean the temperature and pressure under which a nitroalkane is converted to a nitropolyol in the presence of an aldehyde, an alkaline catalyst and a solvent. These conditions are dependent upon a host of factors including, but not limited to, the nitroalkane, the aldehyde, the alkaline catalyst and the amount of alkaline catalyst and the solvent. Typically the temperature is 20° C. to 100° C., more typically 40° C. to 80° C., and typically the pressure is 0 psi (0 kPa) to 10 psi (69 kPa).

"Catalytic amount" and like terms mean the amount of catalyst required to promote at a desired rate the reaction of a nitroalkane with an aldehyde under alkaline conditions to produce a nitropolyol, or the amount of catalyst required to promote at a desired rate the reaction of a nitropolyol with hydrogen under hydrogenation conditions to produce a nitroalcohol. The amount will vary dependent upon a variety of factors including, but not limited to, the nature of the reagents, the alkaline or hydrogenation conditions, the nature of the catalyst and the like, but typically for the reaction of a nitroalkane with an aldehyde under typical alkaline conditions, the amount of alkaline catalyst is 0.01 to 10 mole percent (mol %), more typically 0.2 to 0.5 mol %. For the reaction of a nitropolyol with hydrogen under typical hydrogenation conditions, the amount of hydrogenation catalyst typically is 1 to 20 mol %, more typically 2 to 5 mol %.

Nitroalkanes, Aldehydes and Nitropolyols

The nitroalkanes that can be used in the practice of this invention include any nitroalkane with two or more hydrogen atoms attached to the carbon atom bearing the nitro group, with nitromethane, nitroethane and nitropropane preferred. These nitroalkanes are readily converted to their corresponding nitropolyols by reaction with an aldehyde under alkaline conditions. For example, 2-nitro-2-methyl-1,3-propanediol is prepared from the reaction of nitroethane and formaldehyde while tris(hydroxymethyl)nitromethane is prepared from the reaction of nitromethane and formaldehyde.

Alkaline and Hydrogenation Catalysts

The conversion of a nitroalkane to a nitropolyol is typically conducted over and in contact with an alkaline catalyst. The alkaline catalyst can be a primary, secondary or tertiary amine, an amine salt, fluoride ion, basic silica or alumina, basic ion exchange resin, metal hydroxide or alkoxide salt. Preferred catalysts are tertiary amines such as trimethylamine, triethylamine and the like.

The conversion of a nitropolyol to a nitroalcohol is conducted over and in contact with a hydrogenation catalyst, typically one comprising one or more of the platinum group or the precious metal group. Representative examples include, but are not limited to, palladium, platinum, iridium, ruthenium, gold, silver and the like. The metals of the platinum group are preferred catalysts, particularly palladium. The catalyst can be supported or unsupported and if the former, any suitable support can be employed, e.g., alumina, silica, carbon, etc. If supported, then the supported catalyst typically comprises 0.05% to 10%, preferably 0.5% to 5%, metal.

Optionally, but preferably, the catalyst is used in combination with a chelating agent such as diethylenetriaminepentaacetic acid (DTPA), ethylenediaminetetraacetic acid (EDTA), N,N'-bis(2-hydroxyethypethylenediamine-N,N'-diacetic acid (HEEDA), N-2-hydroxyethyliminodiacetic acid (HEIDA), nitrilotriacetic acid (NTA), and the like. Based on the weight of the catalyst without support, the amount of chelating agent used on a weight to weight basis is 1:1 to 1.5:1.

Specific Embodiment

Preparation of Tris(Hydroxymethyl)Nitromethane

To a stirred 1-liter round bottom flask equipped with a thermocouple, addition funnel, and reflux condenser is charged 295.3 grams (g) 50% aqueous formaldehyde and 3.0 g triethylamine. To the addition funnel is charged 100.0 g of nitromethane. The nitromethane is added to the flask mixture over 4 hours keeping the temperature below 60° C. by regulating the addition rate. After a 1 hour hold and cooling period, the reaction mixture is analyzed by high pressure liquid chromatography (HPLC) and Karl Fischer titration.

The major components are identified as 60.37% tris(hydroxymethyl)nitromethane (TN), 37.5% water, and 0.33% free formaldehyde.

Dehydroxylation of ANGUS Nitropolyols (Summarized from CRI2011015477)

NEPD was evaluated for its potential to produce NMB (2-nitro-2-methyl-1-butanol) via a reductive dehydroxylation reaction as shown:

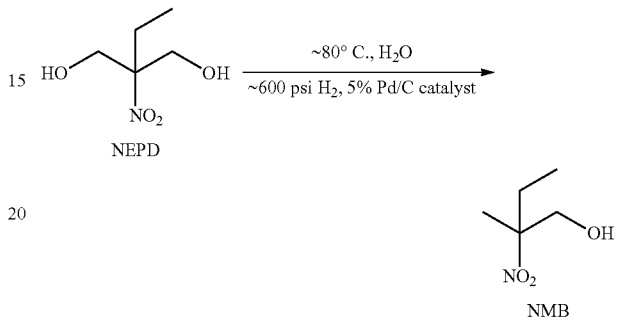

Preparation of NMP and NMPD

TN was evaluated for its potential to produced NMP & NMPD:

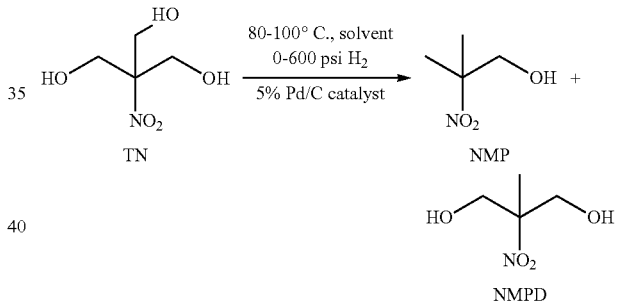

Six experiments were run:
NEPD/DTPA/H$_2$O/Pd—C/600 psig H$_2$/80 C
NEPD/H$_2$O/Pd—C/600 psig H$_2$/80 C
NEPD/H$_2$O/Pd—C/600 psig H$_2$/100 C
TN/H$_2$O/Pd—C/600 psig H$_2$/80 C
TN/MeOH/Pd—C/600 psig H$_2$/80 C
TN/MeOH/Pd—C/600 psig H$_2$/60 C

TABLE 1

| | NEPD Experimental Results | | | | | | | | | | | |
|---|---|---|---|---|---|---|---|---|---|---|---|---|
| | | | | | Product Composition | | | | | | | |
| Time in reactor | | t = 4 hrs | | | | T = 6 hrs | | | | T = 10 hrs | | |
| Reaction | | | | # of | | | | # of | | | | # of |
| Rx # Reaction | NEPD | NMB | Misc | products | NEPD | NMB | Misc | products | NEPD | NMB | Misc | products |
| 1A NEPD/DTPA/H$_2$O/PD—C/600 psi H$_2$/80 C. | 80.5% | 3.6% | 15.9% | 7 | N/A | N/A | N/A | N/A | N/A | N/A | N/A | N/A |

TABLE 1-continued

NEPD Experimental Results

| | | Product Composition | | | | | | | | | | | |
|---|---|---|---|---|---|---|---|---|---|---|---|---|---|
| | Time in reactor | t = 4 hrs | | | | T = 6 hrs | | | | T = 10 hrs | | | |
| Rx # | Reaction | NEPD | NMB | Misc | # of products | NEPD | NMB | Misc | # of products | NEPD | NMB | Misc | # of products |
| 1B | NEPD/H$_2$O/Pd—C/ 600 psi H$_2$/80 C. | 67.4% | 6.0% | 26.6% | 12 | 61.6% | 11.4% | 27.0% | 9 | N/A | N/A | N/A | N/A |
| 1C | NEPD/H$_2$O/Pd—C/ 600 psi H$_2$/100 C. (Aq phase product) | N/A | N/A | N/A | N/A | 61.6% | 11.4% | 27.0% | 9 | n/d | 31.1% | 68.9% | 25 |
| 1D | NEPD/H$_2$O/Pd—C/ 600 psi H$_2$/100 C. (Oil phase product) | N/A | N/A | N/A | N/A | 61.6% | 11.4% | 27.0% | 9 | n/d | 40.2% | 59.7% | 25 |

Notes:
1 N/D indicates not detectable
2 N/A indicates analysis was not applicable for that trial GC analysis of the NEPD series of reactions shows the desired NMB (2-nitro-2-methyl-1-butanol) as the major product.

Presence of DTPA resulted in up to a 40% fewer side products or dissociation products. It also appeared to either slow the progress of the reaction or possibly limit the conversion to the end product.

The increase in reaction temperature may have led to more rapid conversion to NMB and an increased number of dissociation products.

TABLE 2

TN Experimental Results

| | | Product Composition | | | | | | | |
|---|---|---|---|---|---|---|---|---|---|
| | Time in reactor | t = 4 hrs | | | | t = 10 hrs | | | |
| Rx # | Reaction | NMP | NMPD | AMPD | # of products | NMP | NMPD | AMPD | # of products |
| 2A | TN/H$_2$O/Pd—C/600 psi H$_2$/80 C. | 9.2% | N/D | N/A | 16 | 28.9% | N/D | N/A | 17 |
| 2B | TN/MeOH/Pd—C/600 psi H$_2$/80 C. | 9.6% | N/D | N/A | 13 | 32.1% | N/D | N/A | 12 |
| 2C | TN/MeOH/Pd—C/60 psi H$_2$/60 C. | N/A | N/A | 5.4% | 11 | N/A | N/A | 6.0% | 7 |

Notes:
1. N/D indicates not detectable
2 N/A indicates analysis was not applicable for that trial Comparison of results from reactions 2A and 2B shows that the use of MeOH as a solvent, in place of H$_2$O, leads to an approximate 5-10% increase in conversion to the desired end product NMP and fewer (on the order of 20-30%) side reactions (or less dissociation products). This observation seems to be consistent with past experimental observations.

Preparation of 2-Nitro-1-Methylpropanol

To a stirred 2-liter Parr, stainless steel autoclave, is charged 295.6 g deionized water, 3.02 g 5% palladium on carbon catalyst, 1.0 g Ciba-Geigy CHEL DTPA-41 (40% aqueous diethylenetriaminepentaacetic acid pentasodium salt), and 295.6 g 2-nitro-2-methyl-1,3-propanediol (NMPD). The autoclave is sealed, pressure purged three times with nitrogen (N$_2$), three times with hydrogen (H$_2$), and then pressured to and regulated at ~500 psig H$_2$. Agitation is begun and set at 600 revolutions per minute (rpm). Heating is applied with a setpoint to maintain the reactor temperature at 50° C. After 25 minutes and no apparent exotherm, the setpoint is increased to 60° C. The setpoint is incrementally increased to 70° C., 85° C., and 100° C. with no indication of an exothermic reaction. The temperature is maintained at 100° C. for 3 hours. The autoclave is cooled to 60° C., vented, and purged with N$_2$. The reaction product is filtered through a glass microfiber filter to remove catalyst and 512.1 g of filtrate is recovered. The filtrate is analyzed by GC and the major components identified by GC/MS as 38.8 area % 2-nitro-2-methyl-1-propanol (NMP), 9.4 area % 2-nitro-1-propanol, and 21.1 area percent of the starting material (NMPD).

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. A process of preparing a nitroalcohol from a nitropolyol, the process comprising the step of contacting at a temperature of 25-120° C. and a pressure of 300-1400 psi a nitropolyol with hydrogen and a hydrogenation catalyst, wherein the hydrogenation catalyst is Pd/C.

2. The process of claim 1 in which the hydrogenation catalyst is used in combination with a chelating agent.

3. The process of claim 2 in which the chelating agent is at least one of diethylenetriaminepentaacetic acid (DTPA), ethylenediaminetetraacetic acid (EDTA), N,N'-bis(2-hydroxyethyl)ethylenediamine-N,N'-diacetic acid (HEEDA), N-2-hydroxyethyliminodiacetic acid (HEIDA) and nitrilotriacetic acid (NTA).

4. The process of claim 3 in which the amount of chelating agent used on a weight to weight basis with the catalyst metal is 1:1 to 1.5:1.

5. The process of claim 4 in which the nitropolyol is at least one of 2-nitro-2-methyl-1,3-propanediol and tris(hydroxymethyl)nitromethane.

6. A process of preparing a nitroalcohol from a nitroalkane, the process comprising the steps of:
   A) contacting under alkaline conditions a nitroalkane, an aldehyde, and an alkaline catalyst to form a nitropolyol, and
   B) contacting at a temperature of 25-120° C. and a pressure of 300-1400 psi the nitropolyol of step A with hydrogen, a hydrogenation catalyst and, optionally, a chelating agent, wherein the hydrogenation catalyst is Pd/C.

7. The process of claim 6 wherein the nitroalkane is nitromethane or nitroethane.

8. The process of claim 7 wherein the aldehyde is formaldehyde.

9. The process of claim 6 wherein the aldehyde is formaldehyde.

10. The process of claim 6 wherein the amount of alkaline catalyst is 0.01 to 10 mol %.

11. The process of claim 6 wherein the amount of alkaline catalyst is 0.2 to 5 mol %.

12. The process of claim 6 wherein the amount of hydrogenation catalyst is 1 to 20 mol %.

13. The process of claim 6 wherein the amount of hydrogenation catalyst is 2 to 5 mol %.

14. The process of claim 13 wherein the amount of alkaline catalyst is 0.2 to 5 mol %.

15. The process of claim 1 wherein the amount of hydrogenation catalyst is 1 to 20 mol %.

16. The process of claim 3 wherein the amount of hydrogenation catalyst is 1 to 20 mol %.

* * * * *